(12) United States Patent
Wu et al.

(10) Patent No.: US 8,389,039 B2
(45) Date of Patent: Mar. 5, 2013

(54) PROCESS FOR PREPARING BIOACTIVE PROTEIN-ENRICHED WHEY PRODUCTS

(75) Inventors: Chao Wu, Pleasanton, CA (US); Tedd Struckmeyer, Turlock, CA (US)

(73) Assignee: Hilmar Cheese Company, Hilmar, CA (US)

( * ) Notice: Subject to any disclaimer, the term of this patent is extended or adjusted under 35 U.S.C. 154(b) by 316 days.

(21) Appl. No.: 12/366,343

(22) Filed: Feb. 5, 2009

(65) Prior Publication Data
US 2009/0143278 A1 Jun. 4, 2009

Related U.S. Application Data

(62) Division of application No. 10/806,053, filed on Mar. 22, 2004, now abandoned.

(51) Int. Cl.
A23C 21/00 (2006.01)
(52) U.S. Cl. .................. 426/583; 426/580; 426/491
(58) Field of Classification Search ............... 426/478, 426/490, 491, 580, 583, 656, 657
See application file for complete search history.

(56) References Cited

U.S. PATENT DOCUMENTS

| | | | |
|---|---|---|---|
| 3,687,682 | A | 8/1972 | Scheder |
| 5,866,418 | A | 2/1999 | Ballard et al. |
| 6,319,522 | B1 | 11/2001 | Ballard et al. |
| 2002/0044998 | A1 | 4/2002 | Wu |
| 2005/0208638 | A1 | 9/2005 | Wu et al. |
| 2005/0220953 | A1* | 10/2005 | Lihme .................. 426/491 |

OTHER PUBLICATIONS

Kosikowski, F., Cheese and Fermented Milk Foods, Second Edition, 1977, Edwards Brothers, Inc., p. 523.*
Gillies, M.T., Whey Processing and Utilization, 1974, Noyes Data Corporation, p. 28.*
Potter, N.N., Food Science, Third Edition, 1978, AVI Publishing Company, Inc., pp. 407 and 408.*
Sutherland, B.J., Control of salt absorption and whey drainage in cheddar cheese manufacture, The Australian Journal of Dairy Technology, Jun. 1974, p. 86-93.*
"U.S. Appl. No. 10/806,053, Final Office Action mailed Feb. 22, 2008", 5 pgs.
"U.S. Appl. No. 10/806,053, Non Final Office Action mailed May 30, 2007", 5 pgs.
"U.S. Appl. No. 10/806,053, Non-Final Office Action mailed Sep. 5, 2008", 5 pgs.
"U.S. Appl. No. 10/806,053, Response filed Mar. 20, 2007 to Restriction Requirement mailed Feb. 23, 2007", 7 pgs.
"U.S. Appl. No. 10/806,053, Response filed Jul. 29, 2008 to Final Office Action mailed Feb. 22, 2008", 11 pgs.
"U.S. Appl. No. 10/806,053, Response filed Nov. 29, 2007 to Non-Final Office Action mailed May 30, 2007", 27 pgs.
"U.S. Appl. No. 10/806,053, Restriction Requirement mailed Feb. 23, 2007", 6 pgs.
Smithers, G., et al., "New opportunities from the isolation and utilization of whey proteins", *J Dairy Sci.*, 79(8), (Aug. 1996), 1454-9.
Teraguchi, S., et al., "Orally administered bovine lactoferrin inhibits bacterial translocation in mice fed bovine milk.", *Appl Environ Microbiol.*, (Nov. 1995), 4131-4.
Ushida, Y, et al., "Inhibitory effects of bovine lactoferrin on intestinal polyposis in the Apc(Min) mouse", *Cancer Lett.*, 134(2), (Dec. 1998), 141-5.
Yamauchi, K, et al., "Effects of orally administered bovine lactoferrin on the immune system of healthy volunteers", *Adv Exp Med Biol.*, 443, (1998), 261-5.
Blaschek, K. M, et al., "Survey of Salty and Sweet Whey Composition from Various Cheese Plants in Wisconsin", *J. Dairy Sci.*, 90, (2007), 2029-2034.
Elliot, J, et al., "Isolation of lactoferrin and its concentration in sows' colostrum and milk during a 21-day lactation", *J Anim Sci.*, 59(4), (Oct. 1984), 1080-4.
Francis, G., et al., "Extraction from cheese whey by cation-exchange chromatography of factors that stimulate the growth of mammalian cells.", *J Dairy Sci.*, 78(6), (Jun. 1995), 1209-18.
Jin, Y., et al., "Separation, purification, and sequence identification of TGF-beta 1 and TGF-beta 2 from bovine milk.", *J Protein Chem.*, 10(5), (Oct. 1991), 565-75.
Johansson, B., "Isolation of crystalline lactoferrin from human milk.", *Acta Chem Scand.*, 230, (1969), 683-4.
Kakuta, I, et al., "Enhancement of teh nonspecific defense activity of the skin mucus of red sea bream by oral administration of bovine lactoferrin", *Paper*, Department of Biotechnology, Senshu Univerity of Ishnomaki, (1995), 197-202.
Kuwata, T., et al., "Effects of desalting and defatting on the gelling and foaming properties of whey protein.", *Journal of Japanese society of Food Science and Techonology*, 32(9), (1985), 639-645.
Law, B. A., et al., "The isolation and bacteriostatic properties of lactoferrin from bovine milk whey.", *J Dairy Res.*, 44(3), (Oct. 1977), 595-9.
Morrison, M., "Lactoperoxidase. II. Isolation.", *J Biol Chem.*, 238, (Aug. 1963), 2843-9.
Panesar, Parmjit S., et al., "Bioutilisation of whey for lactic acid production", *Food Chemistry*, 105(1), (2007), 1-14.
Parodi, P., et al., "A role for milk proteins in cancer prevention", *Australian J. of Dairy Technology*, (1998), 37-47.
Roberts, "Supplementation of an adapted formula with bovine lactoferrin: 1. Effect on the infant faecal flora.", *Acta Paediatr.*, 81(2), (Feb. 1992), 119-24.

*Primary Examiner* — Leslie Wong
(74) *Attorney, Agent, or Firm* — Schwegman Lundberg & Woessner, P.A.

(57) ABSTRACT

The present invention involves the discovery that various liquid (whey) streams drained or expelled from cheese curd after salt addition in the preparation of cheese contain enriched levels of bioactive proteins such as lactoferrin, lactoperoxidase, immunoglobulins, and growth factors. According to the invention, these proteins may be further enriched through manipulation of the cheese salting process as described herein. The methods of the invention may be used to produce various whey products with enriched levels of all the above bioactive proteins present and, through manipulation of salting conditions, to enrich these proteins selectively.

8 Claims, 2 Drawing Sheets

PROCESS FOR PREPARING BIOACTIVE PROTEIN-ENRICHED WHEY PRODUCTS

CROSS-REFERENCE TO RELATED APPLICATIONS

This application is a divisional of U.S. application Ser. No. 10/806,053, filed on Mar. 22, 2004, now abandoned, and entitled "PROCESS FOR PREPARING BIOACTIVE PROTEIN-ENRICHED WHEY PRODUCTS", which is incorporated herein by reference in its entirety.

BACKGROUND OF THE INVENTION

The proteins present in milk, colostrum, whey, and other such compositions produced from lactating animals, are of great value. They have unique nutritional and functional properties and are often used as ingredients in processed and prepared foods, as well as nutritional supplements and even pharmaceutical formulations. These proteins are generally categorized into two classes. The first class is a heterogenous mixture called casein and represents approximately 80% of the proteins found in milk compositions. The second class is a heterogenous mixture called whey proteins comprising the remaining 20% of the proteins in milk.

Human milk and bovine colostrum contain many bioactive whey proteins, such as lactoferrin (Lf), lactoperoxidase (Lp), immunoglobulins (Ig) and several growth factors. Bovine milk also contains these bioactive components, but at much lower levels than human milk and bovine colostrum.

Large amount of research have been carried out in studying the biological properties of these bioactive proteins from milk and whey. Harper (2000) has reviewed extensively research on many aspects of the potential benefits of these proteins. These bioactive proteins have been shown to possess many biological activities. For example, bioactive proteins from milk and whey such as immunoglobulins, lactoferrin, and lactoperoxidase, all have various types of anti-microbial activities. Bioactive proteins from milk and whey such as lactoferrin, transforming growth factor-$\beta$ (TGF-$\beta$), and immunoglobulins have immune-modulation or immune enhancing effects. Bioactive proteins such as growth factors in whey have been shown to stimulate growth of tissue and cultured cells. There is increasing evidence that some bioactive proteins from milk and whey may have therapeutic value in the treatment of different types of cancer.

Researchers have employed techniques involving various types of chromatography to extract or purify the bioactive proteins from milk. For example, Morrison et al. (1963), Johansson (1969), Law and Reiter (1977) and Elliot et al. (1984) describe ways to extract lactoferrin or lactoperoxidase from various milk sources using cation exchange chromatography. Jin et al. (1991) and Francis et al. (1995) describe methods to extract growth factors from milk or whey using cation-exchange chromatography as the major step.

There are many patents related to extraction, purification, or enrichment of bioactive proteins from milk. For instance, Peyrouset et al. (U.S. Pat. No. 4,436,658) describe a process employing a weakly cation-exchange medium to isolate lactoferrin, lactoperoxidase, and immunoglobulins from whey. Okonogi et al. (U.S. Pat. No. 4,791,193) describe a process, also using cation-exchange medium, to produce high purity lactoferrin from skim milk or whey. Uchida et al. (U.S. Pat. No. 5,516,675) isolated lactoperoxidase, secretory component and lactoferrin from skim milk or whey using a cation-exchange resin. Ballard et al. (U.S. Pat. Nos. 5,866,418, 6,447,808) and Read et al. (U.S. Pat. No. 6,183,784) describe various pharmaceutical uses of milk extracts with high levels of growth factors or growth promoting activities made by cation-exchange chromatography of milk or whey. Kivits et al. (WO 01/25276) describe extracting transforming growth factor-$\beta$ (TGF-$\beta$), insulin-like growth factor (IGF-1), lactoperoxidase and immunoglobulins from skim milk or whey using cation-exchange chromatography and then separating them by a hydroxyapatite column. Maubois (WO 03/006500) describe a process to enrich TGF-$\beta$, which process involves first treating milk serum protein solution at pH4-5.5 and 55-68° C. and then microfiltering the treated solution to obtain a TGF-$\beta$ enriched retentate.

All of the above processes start with milk, whey, a combination or fraction thereof, and employ costly chromatographic or membrane processes to concentrate and/or purify bioactive proteins. The high cost of isolation and purification of these bioactive proteins hinders their commercial utilization. As can be seen, a need exists in the art for simple processes for isolating bioactive proteins from milk components.

SUMMARY OF THE INVENTION

The present invention involves manipulation of the cheese salting process to obtain a product that is enriched in bioactive proteins. According to the invention, the cheese manufacturing process is used as a way to concentrate bioactive proteins from milk, similar to an ion-exchange chromatographic process.

In one embodiment of the invention, a method is provided for preparing a salt whey protein product comprising removing fat from salt whey to provide clarified salt whey and removing salt from the clarified salt whey to provide the salt whey protein product, wherein the salt whey protein product comprises a bioactive protein. In another embodiment of the invention, a method is provided for preparing a salt whey protein product comprising (a) recovering a curd product from a solution comprising coagulated milk; (b) contacting the curd product with salt to provide salted curd and at least one liquid stream comprising salt whey, wherein the salt comprises up to 10% w/w of curd weight; (c) recovering at least one liquid stream comprising salt whey; and (d) concentrating the salt whey to provide the salt whey protein product, wherein the product is enriched for a target bioactive protein. Also provided are products prepared by such methods, including a human nutritional product, a personal care product, a health care product, an animal nutritional product, and a biological product.

DETAILED DESCRIPTION OF THE INVENTION

Figure 1A:
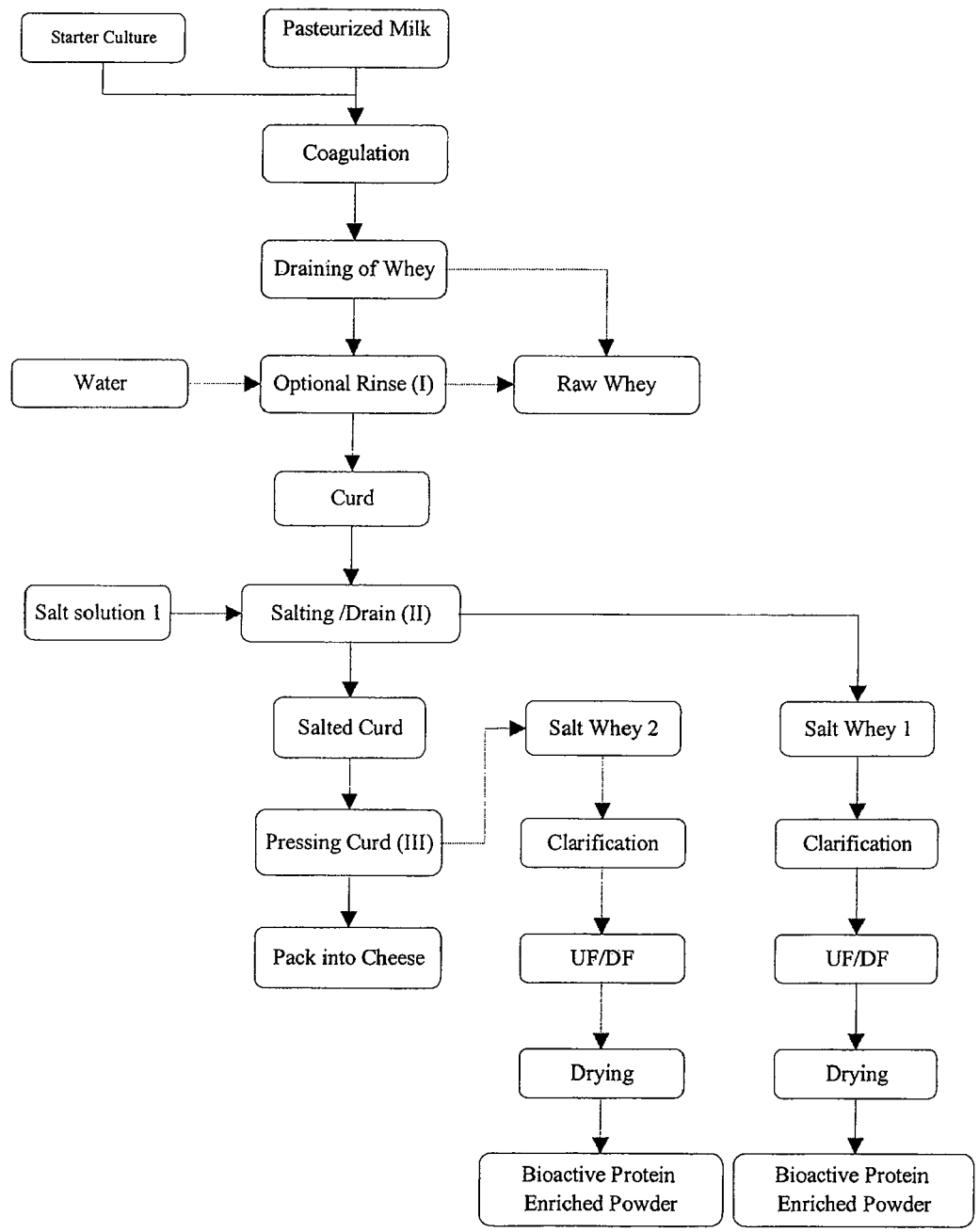
FIGS. 1A and 1B are flow diagrams depicting the preparation of bioactive protein enriched salt whey products according to methods of the invention.

During the process of cheese manufacturing, casein and fat present in the milk starting material form the cheese curd. Whey, which contains the major whey proteins and lactose, is drained from the cheese curd. Salt is then added to the cheese curd to improve the flavor, control microbial metabolism, and expel moisture from the curd. The liquid expelled from cheese curd after salt addition is referred to as salt whey. Traditionally, "salt whey" is often either mixed with the bulk of the whey to be further processed into whey products, or segregated from the bulk of the whey and disposed as waste.

It has been discovered by the present inventors that salt whey is enriched for many bioactive proteins, such as lactoferrin, lactoperoxidase, immunoglobulin, and growth factors, e.g., TGF-β, and IGF-1, as compared to the levels of these bioactive proteins in whey. It was also discovered by the present inventors that a salt whey product, such as salt whey product enriched with one or more of the above-mentioned bioactive proteins can be made without the costly and time consuming need for complicated fractionation processes. All previous methods of purifying and enriching various bioactive proteins from milk or whey involve the use of ion-exchange or microfiltration fractionation processes. The current invention discloses the use of a raw material stream from the cheese manufacturing process, which is enriched in bioactive components. According to the present invention, bioactive protein enriched whey products can be made without using the processes of ion-exchange and/or membrane fractionation, resulting in lower product cost and much greater efficiency.

The present inventors also have discovered that during cheese manufacture, the cheese salting process can be manipulated so as to target one or more bioactive proteins and provide a selectively enriched salt whey protein product.

According to the methods of the invention, salt whey is collected from any cheese manufacturing process and is retained. The salt whey is first clarified to remove fat using methods known in the art. The clarified (and optionally Pasteurized) salt whey is then concentrated to remove salt and lactose, traditionally by ultrafiltration (UF). The molecular weight cut-offs (MWCO) of the ultrafiltration membranes used in this step are below those of the bioactive proteins intended to recover. In one embodiment of the invention, MWCO the membranes are 3K to 30K. Diafiltration (DF) can also be used to remove most of the salt. The resulting protein product can optionally be dried by freeze-drying or spray drying.

Pharmaceutical compositions comprising the bioactive protein enriched product of the invention can be formulated using standard techniques. These typically involve the combination of the product with a physiologically compatible carrier for administration.

I. Definitions

Unless defined otherwise, all technical and scientific terms used herein shall have their same meaning as commonly understood by one of ordinary skill in the art to which this invention pertains. Although any methods and materials similar or equivalent to those described herein can be used in the practice or testing of the present invention, the preferred methods and materials are described. For purposes of the present invention, the following terms are defined below.

As used herein, the term "biologically active protein," "bioactive protein," "biologically active protein fragment" or "bioactive protein fragment" is any polypeptide or fragment thereof derived from a salt whey solution according to the teaching of this invention that has biological activity, e.g., enzymatic activity, etc. Thus, the term "bioactive protein" refers to a protein having biological activity that may be purified from salt whey according to the teachings and methods herein. This can include but is not limited to, lactoferrin, lactoperoxidase, immunoglobulins, growth factors and the like. The term also includes recombinant proteins that are present in milk starting material for any reason.

"Whey" is used herein as a collective term referring to the serum or watery part of milk that remains after coagulation, which occurs primarily in the production of cheese and cottage cheese. In general, whey is composed of lactose (milk sugar), minerals, vitamins and "whey proteins." For example, milk whey protein is prepared by removing fat and casein from milk, and comprises α-lactalbumin, β-lactoglobulin and whey albumin. β-lactoglobulin (β-lg) constitutes about 50% of the total whey proteins.

"Salt whey" and "salt whey solution" refer to a solution containing salt whey. Cheese production is a biochemical process in which milk is converted to a solid intermediate product known as curd. After an initial liquid by-product, referred to as "whey," "raw whey" or "natural cheese whey," is drained from the curd, a salt is added to remove an additional solution from the curd. The additional solution is referred to as "salt whey." Thus, the term "salt whey" refers to any liquid that is drained and/or expelled from cheese curd after the addition of salt in the preparation of cheese or other such milk-related products that are prepared in a similar manner to cheese.

"Coagulation," as used herein, refers to the conversion of any soluble protein to an insoluble form of the protein.

As used herein, the term "enriched" refers to a composition or fraction wherein an object species has been partially purified such that, on a weight basis, the concentration of the object species is substantially higher than the naturally occurring level of the species in a finished product without fractionation. For example, when processing normal cheese whey into whey protein concentrate (WPC) without any fractionation, 0.1 to 1.0% of the protein in the final WPC product is lactoferrin. Therefore, the "naturally-occurring" level of lactoferrin in WPC is considered to be 0.1 to 1.0% of the protein. The term "naturally-occurring" as used herein as applied to an object refers to the fact that object can be found in nature. For example, a polypeptide or polynucleotide sequence that is present in an organism (including viruses) that can be isolated from a source in nature and which has not been intentionally modified by man in a laboratory, is naturally-occurring.

For example, in one embodiment of the present invention, a salt whey protein product is produced that is enriched for lactoferrin, e.g., the product comprises about 3 to about 20 times the amount of lactoferrin that is typically present in whey or a whey protein product. In another embodiment of the present invention, a salt whey protein product is produced that is enriched for lactoperoxidase, e.g., the product comprises about 2-5 times the amount of lactoperoxidase that is typically found in whey or a whey protein product. In another embodiment of the present invention, a salt whey protein product is produced that is enriched for insulin-like growth factor 1 (IGF-1), e.g., the product comprises about 2-10 times the amount of IGF-1 that is typically found in whey or a whey protein product. In another embodiment of the present invention, a salt whey protein product is produced that is enriched for transforming growth factor β1 (TGF-β1), e.g., the product comprises up to 40 times the amount of TGF-β1 that is typically found in whey or a whey protein product. In another embodiment of the present invention, a salt whey protein product is produced that is enriched for transforming growth factor β2 (TGF-β2), e.g., the product comprises up to 10 times the amount of TGF-β2 that is typically found in whey or a whey protein product. In another embodiment of the present invention, a salt whey protein product is produced that is enriched for immunoglobulin G (IgG), e.g., the product comprises up to 2 times the amount of IgG that is typically found in whey or a whey protein product.

As used herein, the term "milk" shall include any composition capable of being excreted from the mammary gland of a lactating animal. For example, milk from a cow, sheep, goat, buffalo, deer, camel, horse, llama, yak, or any mixture thereof.

As used herein, "substantially pure" means that an object species is the predominant species present (i.e. on a molar basis, it is more abundant than any other individual species in the composition), and preferably as substantially purified fraction is a composition wherein the object species comprises at least about 50% (on a weight basis) of all macromolecular species present. Generally a substantially pure composition will comprise more than about 80-90% of all macromolecular species present in the composition. Most preferably the object species is purified to essential homogeneity (contaminant species cannot be detected in the composition by conventional detection methods) wherein the composition consists essentially of a single macromolecular species.

II. Methods of the Present Invention

The process of cheese manufacture is well known in the art and is described more fully in the references incorporated herein.

Briefly, the starting material for cheese production is milk or concentrated milk suitable for cheese manufacture. After the milk is clotted (coagulated) by the action of clotting enzymes known and standardly used in the art, most of the whey is drained, and a given level of salt is added to the remaining curd.

The level of salt to be added can be determined based on the requirement for cheese production, and could range from about 1% to about 10%. In one embodiment, salt is added in a range of about 1% to about 3% of the cheese weight. To achieve the desired enrichment levels of the bioactive proteins, salt is added after most of the whey (>90%) has been removed from the curd. Although sodium chloride is the most commonly used salt in cheese making, many other salts can be employed in the method of the present invention. Examples of the other salts include, but are not limited to, potassium chloride, ammonium chloride, calcium chloride, sodium citrate, etc.

According to the invention, after salt addition, the salt whey is drained naturally, e.g., through perforated belts or screen, and collected. Various liquid streams can be collected after the salt addition step, and all of which are referred to as salt whey streams, which may be used according to the invention. Additional liquid salt whey may be pressed out by mechanical means from the curd and collected. The salt whey streams may be pooled and processed together to produce a single product with enriched levels of various bioactive proteins. In another embodiment of the invention, at least two salt whey streams can be collected and processed separately into salt whey products having different levels of enriched bioactive proteins of interest (FIG. 1B). For example, salt whey that is naturally drained and that is mechanically pressed out can be processed into two different products. Optionally, salting can be achieved in two steps: a lower level of salt addition and collection of the liquid followed by a higher level of salt addition and collection of liquid. The two liquid streams collected at different salt levels can be processed separately to produce products with selective enrichment of various bioactive proteins.

According to the present invention, the processing of salt whey streams involves filtration, such as nanofiltration or ultrafiltration with proper membrane pore sizes, to remove the salts (and lactose in case of ultrafiltration) into permeate. Retentate of this filtration process can be dried by spray drying or freeze-drying into a powder. The conditions for filtration and drying processes need to be carefully controlled to fully recover the bioactive proteins in the final products.

When processed according to present invention using various salt whey streams, the finished products (such as 60-80% whey protein concentrates) can have about 3 to about 20 times enrichment in lactoferrin, about 2 to about 5 times enrichment in lactoperoxidase, about 2 to about 10 times enrichment in IGF-1, up to 40 times enrichment of TGF-$\beta$1, up to 10 times enrichment in TGF-$\beta$2, and/or up to 2 times enrichment in IgG as compared to the corresponding products made from whey.

Currently, bioactive proteins such as those described herein are obtained from milk using a variety of costly processing techniques. Most of these techniques are based upon chromatographic or membrane fractionation techniques. The following is a list of separation techniques currently used in the art of protein purification from milk products and may be used to recover the salt whey bioactive protein enriched product by the methods of the present invention.

1. Ultrafiltration (UF) designates a membrane separation process driven by a pressure gradient in which components of a liquid are fractionated as a function of their solvated size and structure. In UF, the membrane pore size is large enough to allow some components of a liquid to pass through with the water. For example, when concentrating whey protein using a 10,000 MW cutoff polysulfone membranes, most of the lactose and minerals will pass through the membrane to the permeate, some of the smaller polypeptides will also pass through the membrane, whereas almost 100% of protein and fat will remain in the retentate.

2. Microfiltration (ME) designates a membrane separation process similar to UF but with larger membrane pore size allowing particles in the range of 0.02 to 2 micrometers to pass. The pressure used is generally lower than that of UF process. MF is used in the dairy industry for making low-heat sterile milk as proteins may pass through the membrane but not bacteria.

3. Chromatography. Fractionation may also be accomplished using a variety of chromatographic techniques. The most commonly used chromatographic process for industrial protein fractionation is ion-exchange chromatography. It relies on an inert matrix with charged functional groups to adsorb oppositely charged protein molecules. The pH of the protein feed solution is selected so that the proteins to be adsorbed will be charged oppositely to that of the ion-exchange resin. Following adsorption and separation of the non-adsorbed protein and other components in the original protein feed solution, the adsorbed proteins are eluted with salt solution or by changing the pH so the protein charge properties change.

The following examples are intended to illustrate but not limit the invention.

EXAMPLES

Materials and Methods

HPLC and immunochemical methods were used for the analysis of all the proteins and protein fractions isolated from whey.

$\alpha$-lactalbumin ($\alpha$-la) and $\beta$-lactoglobulin ($\beta$-lg) in all the whey protein products were measured by HPLC with a size-exclusion column (Shodex) using a mobile phase of 6 M urea, 0.1 M phosphate buffer, and 0.1 M sodium sulfate, pH 6.0. The samples are dissolved in 0.1 M phosphate buffer, pH 6.0, containing 6 M urea, 0.1 M sodium sulfate, and 0.2% dithiothreitol (DTT) and heated at 80° C. for 5 minutes to fully denature the proteins.

Immunoglobulin G (IgG) and bovine serum albumin (BSA) were analyzed by the same HPLC column, but under native conditions using a mobile phase of 0.1 M phosphate buffer and 0.1 M sodium sulfate, pH 6.0. IgG was also analyzed using radial immuno diffusion (RID) test from Triple-J Farm (Bellingham, Wash.)

Lactoferrin (Lf) and lactoperoxidase (Lp): HPLC with an ion-exchange column (Mono-S from Pharmacia) was used to measure Lf and Lp in the samples. Samples were dissolved in 0.1 M phosphate buffer, pH 7.0 and lactoferrin and lactoperoxidase were eluted by the phosphate buffer with a 0.05 M to 1.80 M NaCl gradient.

Growth factors IGF-1, TGF-beta1 and TGF-beta2 were measured by ELISA methods. IGF-1 was measured using the test kit and its protocol from R&D Systems (Minneapolis, Minn.). TGF-beta1 and TGF-beta2 were both measured using the test kits and protocols of Emax® ImmunoAssay Systems for TGFβ1 and TGFβ2 from Promega Corporation (Madison, Wis.).

The control whey protein concentrate (WPC) used in the comparison is commercially available (Proliant 8000 Whey Protein Concentrate 80%, Proliant, Inc., Ames Iowa).

Figure 1B:
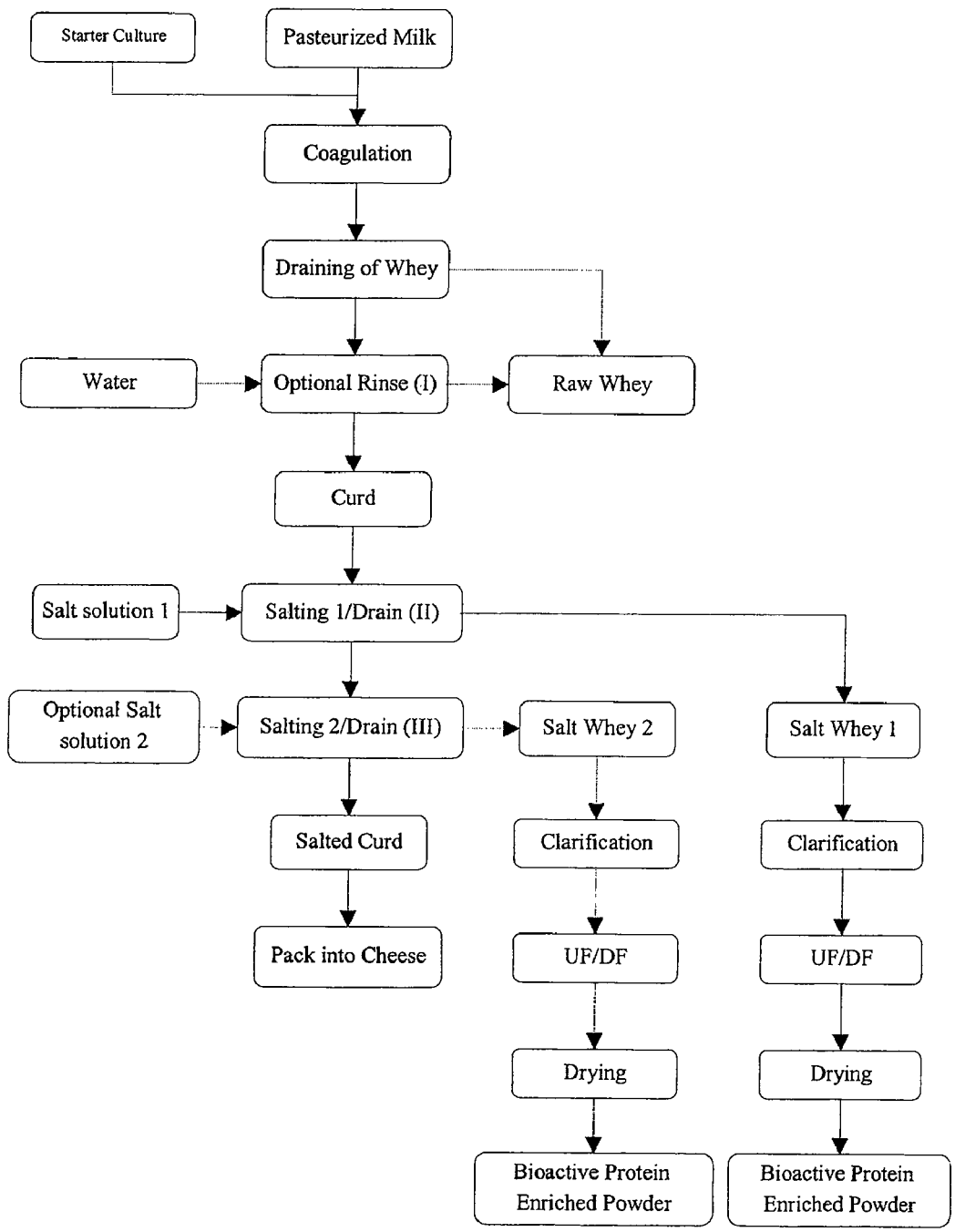

Referring to FIGS. 1 A and B, in the process of cheese manufacture, the starting material is milk. The milk can be Pasteurized, and a starter culture can be added. After the milk has coagulated, most of the whey is drained, and an optional rinse with water is carried out (optional rinse (I) in FIGS. 1A and B). A salt solution can be sprayed onto the curd (salt solution 1 in FIGS. 1A and B). The concentration of salt at this step can be from 0.5% to 10%, e.g., 0.5% to 5%, of the curd weight and is determined based on the type of bioactive proteins that are to be recovered and/or enriched, as well as the requirement of cheese flavor development. After the salt addition, the liquid drained naturally (salting/drain/II, in FIG. 1A) and the liquid pressed out in further cheese process (pressing curd (11) in FIG. 1A) can be pooled and processed together to produce a single product with enriched level of various bioactive proteins. Alternatively, the two liquid stream can be collected and processed separately into two whey products with different levels of enrichment of various bioactive proteins.

Optionally, cheese process and salting processes can be modified to obtain streams of salt whey with selective enrichment of various bioactive proteins. Examples of such modification includes changing the pH at which most of the whey is drained to achieve selective enrichment of desired bioactive proteins, and a two step salting process with a lower level of salt addition and collection of the liquid followed by a higher level of salt addition. The two liquid streams collected at different salt levels can be processed separately to produce products with selective enrichment of various bioactive proteins. For example, a lower level of salt addition and collection of the liquid (salt whey 1 in FIG. 1B) followed by a higher level of salt addition (salt whey 2 in FIG. 1B). Salt whey 1 and salt whey 2 in FIG. 1B are then processed separately to produce products with selective enrichment of various bioactive proteins.

The collected salt whey streams are clarified to remove fat. The clarification can be achieved through centrifugal separation or microfiltration. The clarified (and optionally Pasteurized) streams are concentrated through ultrafiltration (UF) to remove salt and lactose. The molecular weight cut-offs (MWCO) of the membranes are below those of the bioactive proteins of interest, for example, 3K to 30K. Diafiltration (DF) is used to remove most of the salt from the protein product. The product can then be dried by freeze-drying or spray drying.

As discussed herein, the starting material for cheese manufacture is milk, which in one embodiment of the present invention is Pasteurized. In a typical cheese production process, starter culture is added to the milk.

Example 1

Salt whey pressed out in Cheddar cheese process was collected from the tower. The salt whey was centrifuged at 7000×g for 15 minutes at 10° C. to remove fat. After adjusted to pH 6.2 with 6 N NaOH, the separated salt whey was concentrated by ultrafiltration and diafiltration using a bench UF unit with a 10K MWCO spiral-wound membrane cartridge. The final concentrate was freeze-dried into a protein powder (salt whey product A; Table 2).

Example 2

The salt whey streams naturally drained from curd and pressed out in later cheese processing were pooled together and separated by a pilot plant separator (Westfalia SA-7). The separated salt whey was concentrated by ultrafiltration and diafiltration using a pilot plant UF unit with two 10K MWCO spiral-wound membranes. The final concentrate was spray-dried into a protein powder (salt whey product B; Table 2).

Example 3

The salt whey pressed out in cheddar cheese process was collected from the tower. It was separated by a pilot plant separator (Westfalia SA-7). The separated salt whey was concentrated by ultrafiltration and diafiltration using a pilot plant UF unit with two 10K MWCO spiral-wound membranes. The final concentrate was spray-dried into a protein powder (salt whey product C; Table 2).

Example 4

The salt whey naturally drained was collected from cheese belt. It was separated by a pilot plant separator (Westfalia SA-7). The separated salt whey was concentrated by ultrafiltration and diafiltration using a pilot plant UF unit with two 10K MWCO spiral-wound membranes. The final concentrate was spray-dried into a protein powder (salt whey product D; Table 2).

Example 5

The salt whey naturally drained and pressed out in later cheese processing was pooled together. It was separated by a commercial scale separator. A portion of the separated salt whey was concentrated by ultrafiltration and diafiltration using a pilot plant UF unit with two 10K MWCO spiral-wound membranes. The final concentrate was spray-dried into a protein powder (salt whey product E; Table 2).

TABLE 2

Compositions of bioactive protein enriched WPC samples

| Salt Whey Product | Protein % | Ash % | Lf % prot % protein | Lp % prot % protein | IgG % protein | IGF1 ng/g protein | TGF-β1 ng/g protein | TGF-β2 ng/g protein |
|---|---|---|---|---|---|---|---|---|
| A | 63.65 | 8.03 | 32.05 | 0.84 | 4.45 | 284 | 6045 | 881 |
| B | 67.19 | 1.81 | 17.92 | 0.64 | 5.34 | 532 | 4639 | 3073 |
| C | 62.31 | 3.00 | 13.63 | 0.74 | 4.94 | 794 | 4872 | 2648 |
| D | 62.26 | 1.48 | 20.03 | 0.05 | 5.27 | 223 | 7295 | 2435 |
| E | 73.16 | 1.73 | 25.35 | 0.65 | 5.95 | 202 | 8188 | 2008 |
| Control WPC | 76-80 | 2.5-5 | <0.5 | <0.1 | 3-5 | 177 | 150 | 160 |

Example 6

In the cheese manufacturing process, after the milk is coagulated and the whey is drained, water of up to 100% of the curd weight is sprayed onto the curd. The liquid is drained and combined with regular whey. Salt is added at 1% to 10% of curd weight after most of the liquid is drained. The salt whey that is naturally drained and pressed out in later cheese processing is then pooled together, separated by a separator, and concentrated by ultrafiltration and diafiltration with 10K MWCO spiral-wound membranes. The final concentrate is spray-dried into a protein powder. Such a salt whey product is expected to have up to 3 times enrichment of all the bioactive protein listed in Table 2 compared to the samples A-E produced in Examples 1-5.

Example 7

In the cheese manufacturing process, after the milk is coagulated and the whey is drained, a salt solution of up to 100% of the curd weight is sprayed onto the curd. The concentration of the salt solution is such that it will provide an equivalent of up to 2% of the curd weight of salt (NaCl). The liquid drained after this first salt solution rinse is collected as Salt Whey A. Once most of salt whey A is drained, a powdered salt is added to the curd at up to 10% of curd weight. The liquid drained and pressed out after the second salt addition is pooled together and collected as Salt Whey B. Both Salt Whey A and Salt Whey B are separated by a separator and concentrated by ultrafiltration and diafiltration with 10K MWCO spiral-wound membranes. The two final concentrates can be spray-dried into two protein powders, SWP A and SWP B, respectively. Compared to the bioactive protein compositions of samples made in example 1-5 (Table 2), SWP A is expected to have increased levels of IgG and Lp, but a reduced level of Lf, whereas SWP B is expected to have decreased levels of IgG and Lp, but a much increased level of Lf. Depending on the amount of salt used in the first addition, either to SWP A or SWP B, can be selectively enriched for growth factors IGF-1, TGFβ1 and TGFβ2 as compared to samples A-E in example 1-5.

References

Morrison, M., and Hultquist, D. E. 1963. Lactoperoxidase. II. Isolation. J. Biol. Chem. 238(8), 2847-2847.

Harper, J. 2000. Biological Properties of Whey Components, A Review. American Dairy Products Institute.

Johansson, B. G. 1969. Isolation of crystalline lactoferrin from human milk. Acta Chem. Scan. 23, 683.

Law B. A. and B. Reiter 1977. The isolation and bacteriostatic properties of lactoferrin from bovine milk whey. J. Dairy Res. 44, 595.

Elliot, J. I., Senft, B., Erhardt, G., and Fraser, D. 1984. Isolation of lactoferrin and its concentration in sows' colostrum and milk during a 21-day lactation. J. Animal Sci. 59(4), 1080-1084.

Jin, Y., Cox, D. A., Knecht, R., Raschdorf, F., and Cerletti, N. 1991. Separation, purification and sequence identification of TGF-β1 and TGF-β2 from bovine milk. J. Protein Chem. 10(5), 565-575.

Francis, G. L., Regester, G. O., Webb, H. A., and Ballard, F. J. 1995. Extraction from cheese whey by cation-exchange chromatography of factors that stimulate the growth of mammalian cells. J. dairy Sci. 78, 1209-1218.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a bioactive protein enriched whey product comprising:
    a. removing >90% of the whey from a solution comprising coagulated milk;
    b. recovering a curd product from said coagulated milk;
    c. contacting the curd product with salt to provide salted curd and at least one liquid salt whey stream enriched with bioactive proteins, wherein the salt comprises up to 10% w/w of curd weight;
    d. recovering at least one liquid salt whey stream enriched with bioactive proteins; and
    e. concentrating the liquid salt whey stream to provide the bioactive protein enriched whey product;
    wherein the bioactive protein enriched whey product comprises about 3 to about 20 times the amount of lactoferrin that is typically present in whey or a whey protein product; up to 40 times the amount of TGF-β1 that is typically found in whey or a whey protein product; and up to 10 times the amount of TGF-β2 that is typically found in whey or a whey protein product.

2. The method of claim 1, wherein the bioactive protein is concentrated from the curd product following contact with the salt, wherein the salt is present at up to 2% w/w of curd weight.

3. The method of claim 1, further comprising contacting the salted curd with additional salt, and recovering a second liquid salt whey stream enriched with bioactive proteins.

4. The method of claim 1, further comprising modifying the pH of the coagulated milk solution prior to the removal of the whey in step a.

5. The method of claim 1, further comprising removing fat from the recovered liquid salt whey stream enriched with bioactive proteins.

6. The method of claim 1, wherein concentrating the liquid salt whey stream comprises filtration.

7. The method of claim 1 or claim 6, comprising the additional step of
   f. drying the bioactive protein enriched whey product into a powder.

8. The method of claim 1, wherein concentrating the liquid salt whey stream removes salt and lactose from the liquid salt whey stream.

* * * * *